(12) United States Patent
White et al.

(10) Patent No.: US 8,021,307 B2
(45) Date of Patent: Sep. 20, 2011

(54) APPARATUS AND METHOD FOR SENSOR DEPLOYMENT AND FIXATION

(75) Inventors: Jason White, Decatur, GA (US); Kelly Tumlin, Conyers, GA (US)

(73) Assignee: CardioMEMS, Inc., Atlanta, GA (US)

( * ) Notice: Subject to any disclaimer, the term of this patent is extended or adjusted under 35 U.S.C. 154(b) by 1235 days.

(21) Appl. No.: 11/180,840

(22) Filed: Jul. 13, 2005

(65) Prior Publication Data

US 2006/0200030 A1 Sep. 7, 2006

Related U.S. Application Data

(60) Provisional application No. 60/658,358, filed on Mar. 3, 2005, provisional application No. 60/662,210, filed on Mar. 14, 2005.

(51) Int. Cl.
*A61B 5/02* (2006.01)

(52) U.S. Cl. .......... 600/486; 600/485; 600/481

(58) Field of Classification Search .......... 600/485–486
See application file for complete search history.

(56) References Cited

U.S. PATENT DOCUMENTS

| | | |
|---|---|---|
| 2,769,863 A | 6/1957 | Von Wittem |
| 3,867,950 A | 2/1975 | Fischell |
| 3,942,382 A | 3/1976 | Hok |
| 3,958,558 A | 5/1976 | Dunphy et al. |
| 4,026,276 A | 5/1977 | Chubbuck |
| 4,127,110 A | 11/1978 | Bullara |
| 4,206,762 A | 6/1980 | Cosman |
| 4,207,903 A | 6/1980 | O'Neil |
| RE30,366 E | 8/1980 | Rasor et al. |
| 4,237,900 A | 12/1980 | Schulman et al. |
| 4,354,506 A | 10/1982 | Sakaguchi et al. |
| 4,378,809 A | 4/1983 | Cosman |
| 4,485,813 A | 12/1984 | Anderson et al. |
| 4,494,950 A | 1/1985 | Fischell |
| 4,521,684 A | 6/1985 | Gilby et al. |
| 4,596,563 A | 6/1986 | Pande |
| 4,713,540 A | 12/1987 | Gibly et al. |
| 4,718,425 A | 1/1988 | Tanaka et al. |
| 4,796,641 A | 1/1989 | Mills et al. |
| 4,815,472 A | 3/1989 | Wise et al. |
| 4,846,191 A | 7/1989 | Brockway et al. |

(Continued)

FOREIGN PATENT DOCUMENTS

CA 1158061 6/1983

(Continued)

OTHER PUBLICATIONS

A. Dehennis, K.D. Wise; "A Passive-Telemetry-Based Pressure Sensing System": NSF Engineering Research Center for Wireless Integrated Microsystems; Department of Electrical Engineering and Computer Science; The University of Michigan, Ann Arbor, MI 48109-2122 US.

(Continued)

*Primary Examiner* — Patricia C. Mallari
*Assistant Examiner* — Michael D'Angelo
(74) *Attorney, Agent, or Firm* — Ballard Spahr LLP (57) ABSTRACT

A delivery system for fixation of an implant assembly having an intracorporeal device at a deployment site using an anchoring structure. This invention provides an implant assembly having a an anchor for fixation within a vessel. The anchoring structure adapted to be delivered via a catheter.

26 Claims, 8 Drawing Sheets

U.S. PATENT DOCUMENTS

| | | | |
|---|---|---|---|
| 4,890,623 | A | 1/1990 | Cook et al. |
| 4,899,752 | A | 2/1990 | Cohen |
| 4,913,147 | A | 4/1990 | Fahlstrom et al. |
| 4,934,369 | A | 6/1990 | Maxwell |
| 4,987,897 | A | 1/1991 | Funke |
| 5,113,868 | A | 5/1992 | Wise et al. |
| 5,115,128 | A | 5/1992 | Cook |
| 5,129,394 | A | 7/1992 | Mehra |
| 5,165,289 | A | 11/1992 | Tilmans |
| 5,181,423 | A | 1/1993 | Philipps et al. |
| 5,192,314 | A | 3/1993 | Daskalakis |
| 5,207,103 | A | 5/1993 | Wise et al. |
| 5,265,606 | A | 11/1993 | Kujawski |
| 5,353,800 | A | 10/1994 | Pohndorf et al. |
| 5,373,852 | A | 12/1994 | Harrison et al. |
| 5,411,551 | A | 5/1995 | Winston et al. |
| 5,431,171 | A | 7/1995 | Harrison et al. |
| 5,440,300 | A | 8/1995 | Spillman, Jr. |
| 5,487,760 | A | 1/1996 | Villafana |
| 5,497,099 | A | 3/1996 | Walton |
| 5,515,041 | A | 5/1996 | Spillman, Jr. |
| 5,535,752 | A | 7/1996 | Halperin et al. |
| 5,538,005 | A | 7/1996 | Harrison et al. |
| 5,551,427 | A | 9/1996 | Altman |
| 5,566,676 | A | 10/1996 | Rosenfeldt et al. |
| 5,593,430 | A | 1/1997 | Renger |
| 5,600,245 | A | 2/1997 | Yamamoto et al. |
| 5,626,630 | A | 5/1997 | Markowitz et al. |
| 5,686,841 | A | 11/1997 | Stolarczyk et al. |
| 5,695,155 | A | 12/1997 | Macdonald et al. |
| 5,702,427 | A | 12/1997 | Ecker et al. |
| 5,703,576 | A | 12/1997 | Spillman, Jr. et al. |
| 5,713,917 | A | 2/1998 | Leonhardt et al. |
| 5,722,414 | A | 3/1998 | Archibald et al. |
| 5,723,791 | A | 3/1998 | Koch et al. |
| 5,743,267 | A | 4/1998 | Nikolic et al. |
| 5,796,827 | A | 8/1998 | Coppersmith et al. |
| 5,807,265 | A | 9/1998 | Itoigawa et al. |
| 5,836,886 | A | 11/1998 | Itoigawa et al. |
| 5,860,938 | A | 1/1999 | Lafontaine et al. |
| 5,899,927 | A | 5/1999 | Ecker et al. |
| 5,935,084 | A | 8/1999 | Southworth |
| 5,942,991 | A | 8/1999 | Gaudreau et al. |
| 5,967,986 | A | 10/1999 | Cimochowski et al. |
| 6,015,386 | A | 1/2000 | Kensey et al. |
| 6,015,387 | A | 1/2000 | Schwartz et al. |
| 6,019,729 | A | 2/2000 | Itoigawa et al. |
| 6,024,704 | A | 2/2000 | Meador et al. |
| 6,025,725 | A | 2/2000 | Gershenfeld et al. |
| 6,030,413 | A | 2/2000 | Lazarus |
| 6,033,366 | A | 3/2000 | Brockway et al. |
| 6,053,873 | A | 4/2000 | Govari et al. |
| 6,076,016 | A | 6/2000 | Feierbach |
| 6,111,520 | A | 8/2000 | Allen et al. |
| 6,113,553 | A | 9/2000 | Chubbuck |
| 6,134,461 | A | 10/2000 | Say et al. |
| 6,140,740 | A | 10/2000 | Porat et al. |
| 6,159,156 | A | 12/2000 | Van Bockel |
| 6,198,965 | B1 | 3/2001 | Penner et al. |
| 6,201,980 | B1 | 3/2001 | Darrow et al. |
| 6,206,835 | B1 | 3/2001 | Spillman, Jr. et al. |
| 6,237,398 | B1 | 5/2001 | Porat et al. |
| 6,239,724 | B1 | 5/2001 | Doron et al. |
| 6,277,078 | B1 | 8/2001 | Porat et al. |
| 6,278,379 | B1 | 8/2001 | Allen et al. |
| 6,287,253 | B1 | 9/2001 | Ortega et al. |
| 6,373,264 | B1 | 4/2002 | Matsumoto et al. |
| 6,409,674 | B1 | 6/2002 | Brockway et al. |
| 6,416,474 | B1 | 7/2002 | Penner et al. |
| 6,442,413 | B1 | 8/2002 | Silver |
| 6,454,720 | B1 | 9/2002 | Clerc et al. |
| 6,645,143 | B2 | 11/2003 | VanTessel et al. |
| 6,667,725 | B1 | 12/2003 | Simons et al. |
| 6,765,493 | B2 | 7/2004 | Lonsdale et al. |
| 6,923,769 | B2 | 8/2005 | Nishii et al. |
| 6,926,670 | B2 | 8/2005 | Rich et al. |
| 7,572,228 | B2 * | 8/2009 | Wolinsky et al. ............ 600/486 |
| 2002/0077556 | A1 * | 6/2002 | Schwartz ............ 600/486 |
| 2002/0151816 | A1 | 10/2002 | Rich et al. |
| 2002/0161382 | A1 * | 10/2002 | Neisz et al. ............ 606/151 |
| 2002/0188207 | A1 | 12/2002 | Richter |
| 2003/0031587 | A1 | 2/2003 | Hu et al. |
| 2003/0125790 | A1 | 7/2003 | Fastovsky et al. |
| 2003/0136417 | A1 | 7/2003 | Fonseca et al. |
| 2003/0139677 | A1 | 7/2003 | Fonseca et al. |
| 2003/0216622 | A1 * | 11/2003 | Meron et al. ............ 600/300 |
| 2004/0044393 | A1 | 3/2004 | Yarden et al. |
| 2004/0122494 | A1 | 6/2004 | Eggers et al. |
| 2004/0176672 | A1 | 9/2004 | Silver et al. |
| 2005/0075697 | A1 | 4/2005 | Olson et al. |
| 2005/0085703 | A1 | 4/2005 | Behm |
| 2005/0154321 | A1 | 7/2005 | Wolinsky et al. |
| 2005/0187482 | A1 | 8/2005 | O'Brien et al. |
| 2005/0288596 | A1 * | 12/2005 | Eigler et al. ............ 600/485 |
| 2006/0200030 | A1 | 9/2006 | White et al. |
| 2006/0200031 | A1 | 9/2006 | White et al. |
| 2007/0270934 | A1 | 11/2007 | Stern et al. |

FOREIGN PATENT DOCUMENTS

| | | |
|---|---|---|
| DE | 19644858.5 | 10/1996 |
| EP | 0337035 | 11/1993 |
| EP | 0646365 | 4/1995 |
| EP | 1 264 572 A | 12/2002 |
| WO | WO 83/03348 | 10/1983 |
| WO | WO 90/06723 | 6/1990 |
| WO | WO 95/33517 | 12/1995 |
| WO | WO 97/09926 | 3/1997 |
| WO | WO 97/32518 | 9/1997 |
| WO | WO 97/32519 | 9/1997 |
| WO | WO 97/33513 | 9/1997 |
| WO | WO 99/34731 | 7/1999 |
| WO | WO 00/16686 | 3/2000 |
| WO | WO 00/74557 A | 12/2000 |
| WO | WO 01/00089 | 1/2001 |
| WO | WO 01/87137 | 11/2001 |
| WO | WO 01/97908 | 12/2001 |
| WO | WO 2005/067817 A | 9/2002 |
| WO | WO 03/061504 | 7/2003 |
| WO | WO 95/31229 A | 11/2005 |
| WO | 2006/094273 A | 9/2006 |
| WO | 2007/106533 A1 | 9/2007 |

OTHER PUBLICATIONS

S.R. Vallabhane, J. Brennan, G. Gilling-Smith, D. Gould, T. How, R. McWilliams, P.L. Harris; "Aortic Side Branch perfusion Alone Does Not Account for High Intra-Sac Pressure After Endovascular Repair (EVAR) in the Absence of Graft-Related Endoleak"; Royal Liverpool University Hospital, Liverpool, UK.

M. Gawenda, J. Heckenkamp, M. Zaehringer, J. Brunkwall; "Intra-Aneurysm Sac Pressure—The Holy Gail of Endoluminal Grafting of AAA"; Eur J Vasc Endovasc Surg, vol. 24, Aug. 2002, pp. 139-145.

GWH Schurink, NJM Arts, J Wild, J.M Van Baalen, TAM Chutner, LJ Schultze Kool, JH Van Bockel; "Endoleakage After Stent-Graft Treatment of Abdominal Aneurysm: Implications on Pressure and Imaging-An In Vitro Study"; Journal of Vascular Surgery, vol. 28, No. 2, pp. 234-241.

B. Sonesson, N. Dias, M. Malina, P. Olofsson, D. Griffin, B. Lindblad, K. Ivancev; "Intra-Aneurysm Pressure Measurements in Successfully Excluded Abdominal Aortic Aneurysm After Endovascular Repair"; Journal of Vascular Surgery, vol. 37, No. 4, Apr. 2003, pp. 733-738.

C.S. Skillern, S.L. Stevens, K.T. Piercy, R.L. Donnell, M.B. Freeman, M.H. Goldman; "Endotension in an Experimental Aneurysm Model"; Journal of Vascular Surgery, vol. 36, No. 4, Oct. 2002, pp. 814-817.

G.D. Treharne, I.M. Loftus, M.M. Thompson, N. Leonard, J. Smith, G. Fishwick, PRF Bell; "Quality Control During Endovascular Aneurysm Repair: Monitoring Aneurysmal Sac Pressure and Superficial Femoral Artery Flow Velocity"; J. Endovasc Surg, 1999, 6, pp. 239-245.

M.L. Manwaring, V.D. Malbasa, K.L. Manwaring: "Remote Monitoring of Intercranial Pressure"; Institute of Concology; Annals of the Academy of Studencia Apr. 2001; pp. 77-80.

GWH Schurink, NJM Arts, J.M Van Baalen, L.J Schultze Kool, JH Van Bockel; "Experimental Study of the Influence of Endoleakage Size on Pressure in the Aneurysm Sac and the Consequences of Thrombosis"; Bristish Journal of Surgery 2002, 87, pp. 71-78.

K. Ouriel; "role of intrasac Pressure Measurements After EVAR: Can They Be Followed Noninvasively?"; Combined Session: Vascular Surgery and Interventional Radiology; VII 4.1.

R.A. Baum, J.P. Carpenter, C. Cope, M.A. Golden, O.C. Velazquez, D.G. Neschis, M.E. Mitchell, C.F. Barker, R.M. Fairman; "Aneurysm Sac Pressure measurements After Endovascular Repair of Abdominal Aortic Aneurysms"; Journal of Vascular Surgery, vol. 33, No. 1, Jan. 2001, pp. 32-41.

P.L. Harris, S. Dimitri; "Predicting failure of endovascular Aneurysm repair"; Eur J Vas Endovasc Surg, vol. 17, Jan. 1999; pp. 1-2.

G. Akingba, A. Cheng, A. Shum, P. Yang; "An Implantable Pressure Sensor for Aneurysmal Disease".

K.F. Adams, Jr.; "Guiding Heart Failure Care by Invasive Hemodynamic Measurements: Possible or Useful?"; Journal of cardiac failure, vol. 8, No. 2, Apr. 2002, pp. 71-73.

A. Magalski, P. Adamson, F. Gadler, M. Boehm, D. Steinhaus, D. Reynolds,K. Vlach, C. Linde, B. Cremers, B. Sparks, T. Bennet; "Continuous Ambulatory Right Heart Presure Measurements with an Implantable Hemodynamic Monitor: A Multicenter, 12-Month Follow-Up Study of Patients with Chronic Heart Failure"; Journal of Cardiac failure, vol. 8, Apr. 2002, pp. 63-70.

R. Shabetai; "Monitoring Heart Failure Hemodynamics with an Implanted Device: Its Potential to Improve Outcome"; Journal of the American College of Cardiology; vol. 41, No. 4, Feb. 19, 2003; pp. 572-573.

J.C. Parodi, R. Berguer, L.M. Ferreira, R. Lamura, M.L. Schererhorn; "intra-eneurysmal Pressure After Incomplete Endovascular Exclusion"; Journal of Vascular Surgery, vol. 24, No. 5, Nov. 2001, pp. 909-914.

M. Gawenda, J. Heckenkamp, S. Winter, G. Jaschke, J. Brunkwall; Pressure if Transmitted Through PTFE and Dacron Grafts Leading the Aneurysm Sac Pressure Endoluminal Grafting of AAA—An In Vitro Study; Vascular Centre, university of Cologne, Germany.

T. Akin, B. Ziaie, K. Najafi; "RF Telemetry Powering and Controlling of Hermetically Sealed Integrated Sensors and Actuators"; Center for Integrated Sensors and Circuits; Department of Electrical Engineering and Computer Science; University of Michigan; Ann Arbor, Michigan 48109-2122; pp. 145-148.

H.E. Haynes, A.L. Witchey; "Medical electronics: The Pill That Talks"; DEP, Camden, N.J.

A. Dehennis, K.D. Wise; "A Double-Sided Single-Chip Wireless Pressure Sensor": Engineering Research Center for Wireless Integrated Microsystems; Department of Electrical Engineering and Computer Science; The University of Michigan, Ann Arbor, MI 48109-2122 US.

J. Zhe, R.R. Farmer, V. Modi; "A MEMS Device for Measurement of Skin Friction with Capacitive Sensing"; Department of Mechanical Engineering, Columbia university, NY 10027; Microelectronics research Center, New Jersey institute of Technology, Newark, NJ 07102.

T. Chuter, K. Ivancev, M. Malina, T, Resch, J. Brunkwall, B. Lindblad, B. Risberg; "Endovascular and Surgical techniques"; Eur J. Vasc Endovasc Surg vol. 13, Jan. 1997, pp. 85-87.

J.T. Farrar, C. Berkley, V.K. Zworykin; "Telemetering of Intraenteric pressure in man by an Externally Energized Wireless Capsule"; Science, New Series, vol. 131, Issue 3416 (Jun. 17, 1960), 1814.

\* cited by examiner

APPARATUS AND METHOD FOR SENSOR DEPLOYMENT AND FIXATION

RELATED APPLICATION DATA

This application claims priority to provisional U.S. Application No. 60/658,358, filed Mar. 3, 2005 and to provisional U.S. Application No. 60/662,210, filed Mar. 14, 2005.

FIELD OF THE INVENTION

This invention relates generally to implantation of intracorporeal devices into vessels, and to fixing the devices, either permanently or temporarily, within the vessel.

BACKGROUND OF THE INVENTION

In recent years, the long-sought goal of implantable biosensors has begun to see realization and, in some cases, clinical use. As this concept has seen continued research and development, issues regarding intracorporeal fixation of the sensor have come to light. Particularly within blood vessels, the sensor is subjected to a continuous, pulsatile flow. This is a difficult environment in which to secure a sensor or other apparatus reliably without unduly restricting blood flow or impairing the vessel wall. One major vessel of interest in the realm of cardiology is the pulmonary artery. The pulmonary artery is a particularly challenging location in which to secure an intracorporeal device because, in addition to the above considerations, the vessel is especially thin, compliant and prone to perforation.

Design considerations for an ideal fixation device intended for intravascular fixation are outlined as follows. The fixation device should be passive and maintain a separation distance between the sensor and the vessel wall. The deployed size and radial strength of the device should be sufficient to prevent its migration into vessels that would be occluded by the dimensions of the sensor while creating minimal stress concentrations where the fixation device contacts the vessel wall. Alternatively, intracorporeal devices can be designed sufficiently small in size so that when deployed in organs or regions with sufficiently redundant blood flow, the device can embolize on its own without harming the organ or the host. Finally, the fixation device should be sufficiently versatile as not to depend, within physiologically relevant ranges, on the size of the vessel in order to maintain its position.

There have been attempts to create devices intended to hold intracorporeal devices fixedly within vessels. Several such attempts are described in patent publication number US 2004/0044393 and in European patent application number EP0928598. These attempts fall short of meeting all of the necessary requirements outlined above.

Prior art devices include a self-expansible stent on which an intracorporeal device is mounted. This stent maintains a known length when implanted in a vessel where only the approximate diameter can be determined. Other devices and methods include fixation of a sensor in a bodily lumen, in which the sensor support is coupled to a fixation device. The fixation device is a stent or ring, has a sensor support coupled thereto and is intended to be sutured to the vessel wall or held in place by plastically deforming the structure using a balloon catheter. The ring is essentially a stent with an abbreviated length and suffers from the same shortcomings as traditional stent devices.

For example, a stent is designed with mechanical characteristics that enable it to hold open diseased vessels post dilation. Therefore, the radial strength of the stent is greater than the inward radial forces exerted during vessel recoil. This primary requirement leads to a mismatch in compliance, with that of the stent dominating. Subsequently, stress concentrations are created at the interface of the stent and vessel. These stress concentrations are greatest at the terminal ends of the stent where there is an abrupt transition in stiffness between the stented and unstented segments of the vessel. As undiseased vessels are usually more compliant compared to diseased ones, this problem is amplified when placing a stent in healthy vasculature. Along similar lines, accurate stent sizing in the vessel is critical, especially in the case of the pulmonary artery. Thus, the physician must be conscious of the particulars of vessel compliance, recoil and stent radial strength in order to choose the best stent expanded diameter for a given vessel. This determination presents its own set of challenges and requires an unnecessary increase in complexity. Therefore, the use of a stent in order to maintain an intracorporeal device in a vessel is not optimal.

Thus, a need exists for devices and methods for fixing intracorporeal devices which satisfy the design requirements described herein. Furthermore, a need exists to deliver and fix such devices in a safe and predictable manner.

SUMMARY OF THE INVENTION

Stated generally, this invention comprises an apparatus and method of deployment and fixation of an implant assembly by using a delivery apparatus to deliver an intracorporeal device to a deployment site and fixation of the device using an anchoring structure. The intracorporeal device may be either a wired or a wireless device.

Thus it is an aspect of this invention to provide an implant assembly having a an anchor for fixation within a vessel.

A further aspect of this invention to provide an anchoring structure adapted to be delivered via a delivery apparatus, such as a catheter.

Other objects, features, and advantages of the present invention will become apparent upon reading the following specification, when taken in conjunction with the drawings and the appended claims.

DETAILED DESCRIPTION

An implant assembly of this invention includes an intracorporeal device and an anchoring structure used to stabilize the intracorporeal device in the body, such as in a vessel. Delivery systems of this invention are used to deploy and secure the implant assembly in a desired location in a vessel and include a delivery apparatus and an implant assembly. The intracorporeal device may be a pressure sensor, further described below. The anchoring structure may be a structure capable of being introduced into the body via a delivery apparatus, such as a catheter, and then lodging within the vessel. Anchoring structures of this invention may be formed from metal or polymer, and may be in the form of a wire structure. Wire structures of this invention may include structure including opposed wire loops, radial wire array structures, and daisy petal structures, all further described below.

All of the implant assemblies of this invention obstruct approximately 50% or less of the cross-sectional area of the vessel in which it resides. Preferably, the implant assemblies obstruct 20% or less of the cross-sectional area of the vessel. Minimizing the obstruction of flow within the vessel allows the sensor to remain secured in position in a vessel without creating significant impact to the flow within the vessel.

The intracorporeal device used to couple to the anchoring structures described below has a width of about 0.5 to about 4 mm, a height of about 0.5 to about 4 mm, and a length of about 0.5 to about 12 mm. In one embodiment, the intracorporeal device has a width of 3.2 mm, a height of 2 mm, and a length of 10 mm. Examples of such devices are disclosed in commonly owned U.S. Pat. No. 6,855,115; and in co-pending, commonly owned applications Ser. Nos. 10/054,671; 10/886,829; 10/215,377; 10/215,379; 10/943,772 incorporated herein by reference.

Wire Loop Structures

Figure 1:
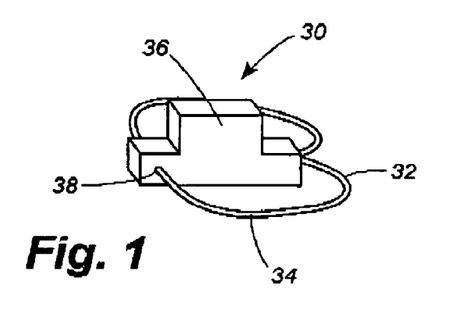
FIG. 1 is an isometric view of a first embodiment of an implant assembly of this invention having two opposed wire loops.
Figure 2:
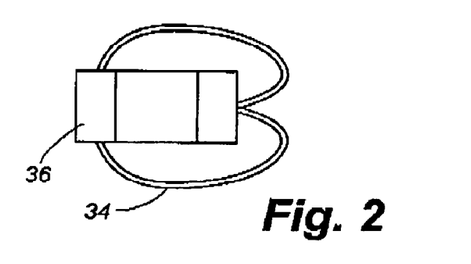
FIG. 2 is a top view of the implant assembly of FIG. 1.
Figure 3:
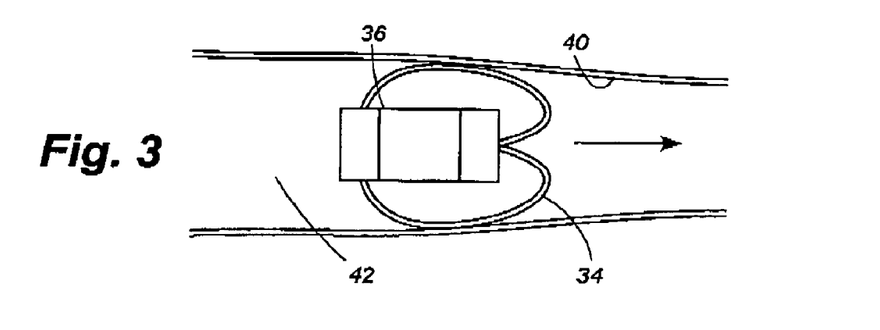
FIG. 3 is a side view of the implant assembly of FIG. 1 fixed in a vessel.

One implant assembly of this invention adapted for deployment and fixation within a vessel includes an intracorporeal device and a wire structure having wire loops. The loops may traverse the length of the device or may be limited to one end of the device. As shown in FIGS. 1-3, one embodiment of an implant assembly 30 having a double loop structure 32 includes a wire 34 attached to an intracorporeal device 36 at an anchor point (not shown). The wire 34 is threaded through an end of the intracorporeal device 36 at a hole 38. The anchor point is formed by crimping a piece of metal to the wire and trimming off the excess wire, so that the crimped-on metal comprises the terminal end of the wire. This metal end also provides a radiopaque marker for fluoroscopic visualization of the device.

After the wire 34 is threaded through the hole 38 on one end of the device, the wire is pulled with sufficient force to bury the anchor fixedly into the silicone coating of the intracorporeal device. The wire 34 is then looped around to form the double loop configuration 32. The second free end is also inserted under the coating and the anchor is buried in the coating to fix the anchor. In this manner, the ends of the wire are inserted under the coating of the intracorporeal device 36 and away from the sensor.

Upon deployment of the implant assembly 30, the wire 34 contacts the inner surface 40 of the wall of the vessel 42, as shown in FIG. 3. The arrow shown in FIG. 3 indicates the direction of blood flow.

Figure 4:
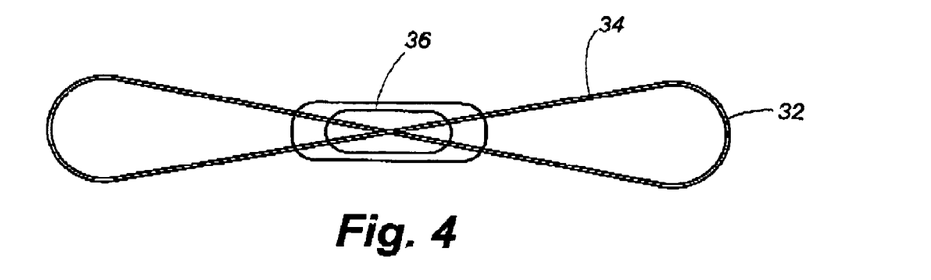
FIG. 4 is a top view of a second embodiment of an implant assembly of the invention having opposed wire loops.
Figure 5:
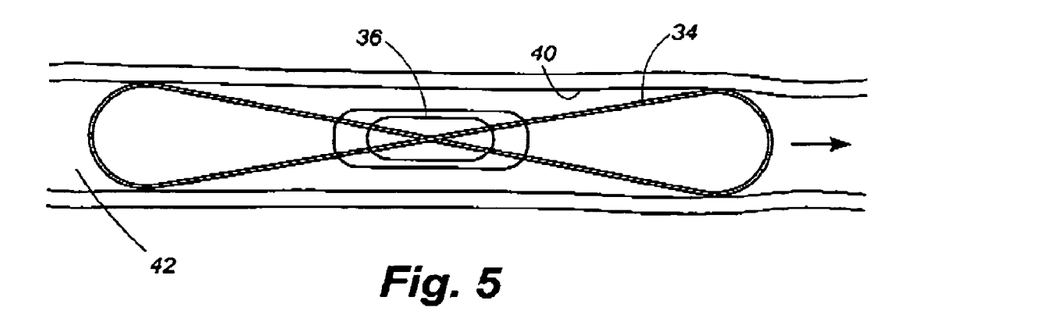
FIG. 5 is a top view of the implant assembly of FIG. 4 fixed in a vessel.

In an alternative embodiment, shown in FIGS. 4 and 5, the loop structure has a "figure eight" shape. Implant assembly 31 having a double loop structure 33 includes a wire 35 attached to sensor body 37 at an anchor point (not shown). The ends of the wire 35 are inserted under the coating of the sensor body 37 and away from the sensor as described in the previous example. Upon deployment of the implant assembly 31, the wire 35 contacts the inner surface 41 of the wall of the vessel 43, as shown in FIG. 5. The arrow shown in FIG. 5 indicates the direction of blood flow.

According to one embodiment, the opposed loop structure is constructed of a single wire. In an alternative embodiment, the opposed loop structure is constructed of more than one wire.

In alternative embodiments, shown in FIGS. 6-8 and 9-11, the structure includes a plurality of wire loops 44 encircling an intracorporeal device 46. The wire 48 is threaded from end to end in a circular fashion, through one or more holes 50 located on each end of the sensor, to form the loops. Upon completion of the loop structure, the free end of the wire is used to create another anchor as described above. The second free end is then pulled back into the silicone coating with sufficient force to bury the second anchor fixedly in the silicone coating. The location of the second anchor lies on the opposite side of the sensor from the first anchor. The wire loops are then arranged by mechanical means to create wire members that are substantially evenly distributed radially around the longitudinal axis of the sensor.

Figure 6:
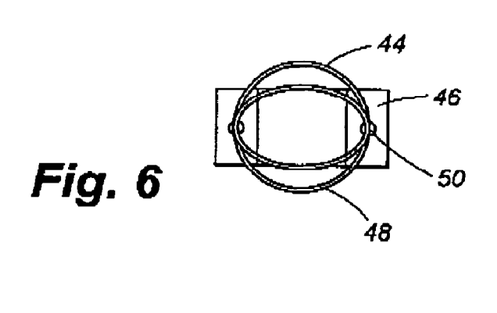
FIG. 6 is a top view of a third embodiment of an implant assembly of this invention having two opposed wire loops.
Figure 7:
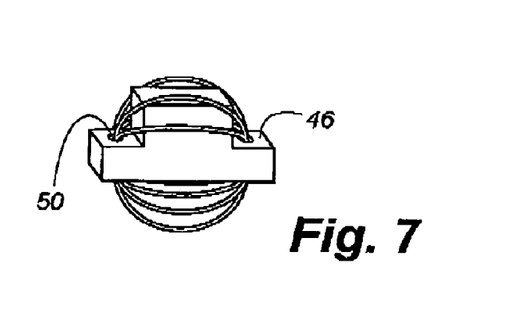
FIG. 7 is an isometric view of the implant assembly of FIG. 6.
Figure 8:
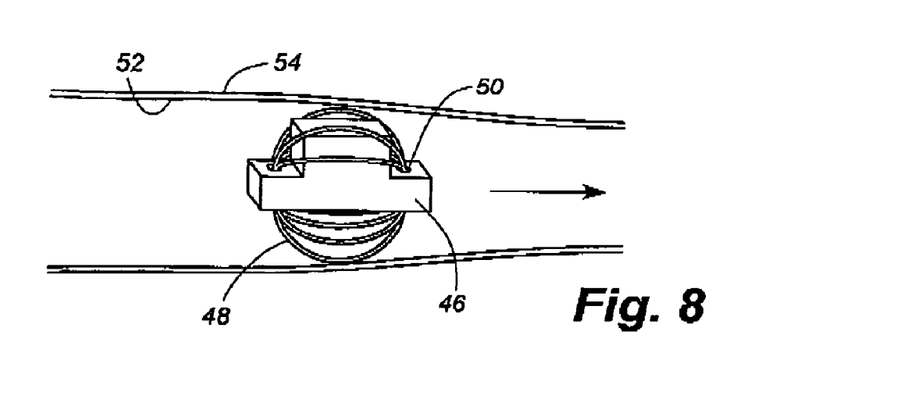
FIG. 8 is an isometric view of the implant assembly of FIG. 6 fixed in a vessel.
Figure 9:
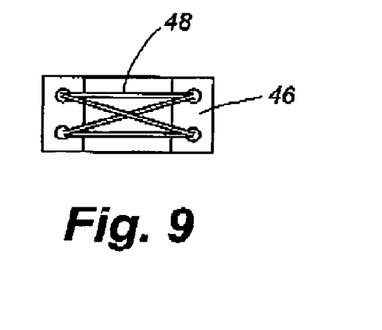
FIG. 9 is a top view of a fourth embodiment of an implant assembly of this invention having opposed wire loops.
Figure 10:
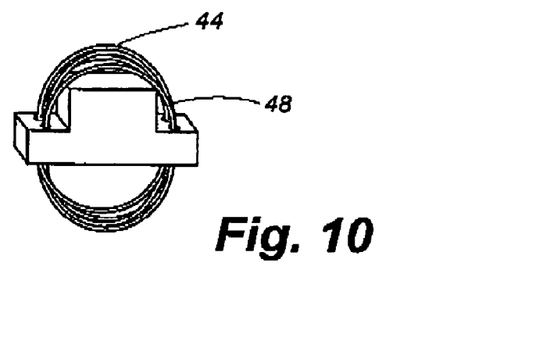
FIG. 10 is an isometric view of the implant assembly of FIG. 9.
Figure 11:
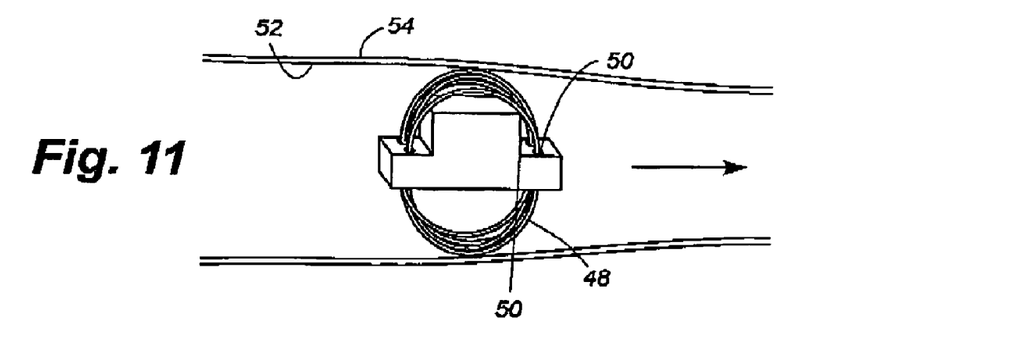
FIG. 11 is an isometric view of the implant assembly of FIG. 9 fixed in a vessel.

The wire loops may be attached to the intracorporeal device 40 by threading through one hole 50 located near the edge of the device 46 as referenced to the longitudinal axis of the device 46, as shown in FIG. 6. Alternatively, the wire loops may be attached to the intracorporeal device 46 by threading through two holes 50 located near each edge of the device 46, as shown in FIG. 9. Upon deployment of the implant assembly, each configuration contacts the inner surface 52 of the wall of the vessel 54, as shown in FIGS. 8 and 11. The arrows shown in FIGS. 8 and 11 indicate the direction of blood flow.

The wire diameter of the anchoring structure lies in the range of about 0.001 to about 0.015 inches. The material comprising the wire can be any biocompatible material known in the art that possess sufficient elastic properties to be useful for the purpose at hand. The material may be a metal, such as nitinol, stainless steel, eligiloy, cobalt chrome alloys, or any other suitable metal. In a further embodiment, the biocompatible wire is coated with a dielectric material, such as, but not limited to, PTFE, polyurethane, parylene and diamond-like carbon (DLC) so as not to pose electromagnetic interference with the function of the intracorporeal device when the device comprises an RF sensor.

Radial Wire Array Structures

Another implant assembly according to this invention includes an intracorporeal device and an anchoring structure having a substantially parabolic-shaped profile, as shown in FIGS. 12-17. As illustrated in the Figures, an implant assembly 58 includes an intracorporeal device 60 and a radial wire array 62, which includes wire members 64. Members 62 may be attached to the intracorporeal device 60 at an anchor point, as described above.

Figure 12:
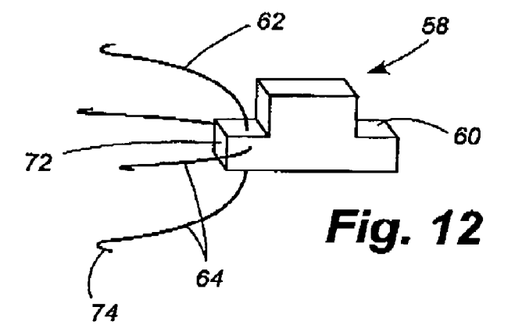
FIG. 12 is an isometric view of a fourth embodiment of an implant assembly of this invention having a radial wire array expansible structure.
Figure 16:
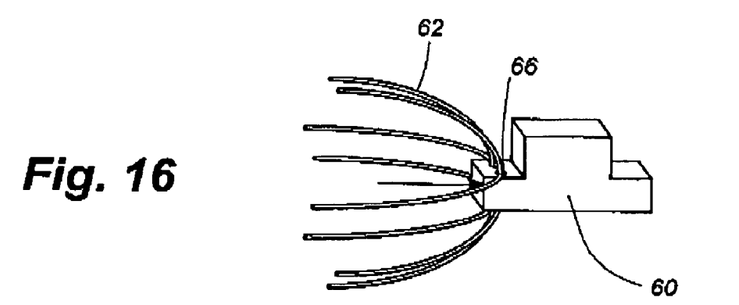
FIG. 16 is an isometric view of a seventh embodiment of an implant assembly of this invention having a radial wire array expansible structure.
Figure 17:
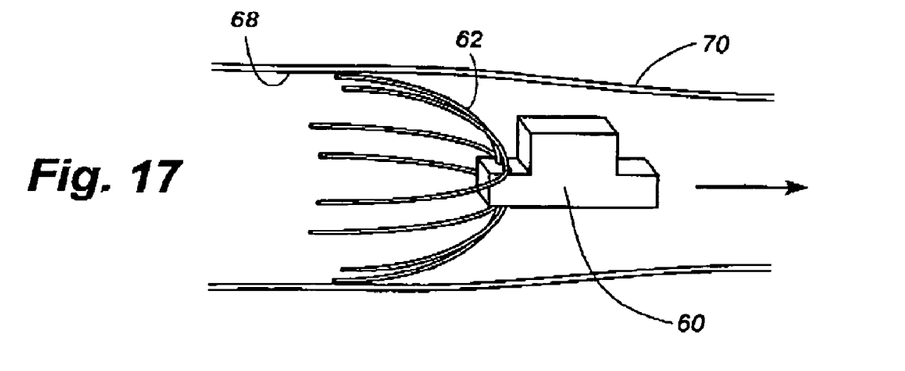
FIG. 17 is an isometric view of the implant assembly of FIG. 16 fixed in a vessel.

The radial wire array 62 can be attached to the intracorporeal device 60 by threading the wire members 64 through one hole 66 located near the edge of the intracorporeal device 60, as shown in FIG. 12. Alternatively, the radial wire array 62 can be attached to the intracorporeal device 60 by threading the wire members 64 through two holes 66 located near the edge of the device 60 as shown in FIG. 16. The wire end is press-fit into a silicone coating covering the surface of the device to secure the end. The radial wire array may be formed by crimping a piece of metal at a point substantially midlength of the wire bundle and then threading the wire bundle through a hole near the edge of the intracorporeal device, thus lodging the anchor within the silicone material filling the hole. The anchor secures the end of the radial wire between the surface of the device and the silicone coating covering the surface of the device. The crimped metal anchor provides a radiopaque marker for fluoroscopic visualization of the device. Upon deployment of the implant assembly, the radial wire array 62 contacts the inner surface 68 of the wall of the vessel 70, as shown in FIGS. 15 and 17.

In one embodiment, the radial wire array is self-supporting, as a result of the physical properties of the material. Alternatively, the radial wire array may include a mechanical expansion structure to support the array to expand and contact the vessel wall. For example, a catheter balloon may be inflated to cause a wire structure to attain and maintain an expanded configuration.

Figure 13:
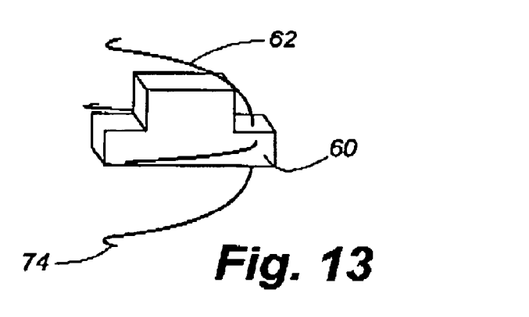
FIG. 13 is an isometric view of a fifth embodiment of an implant assembly having an alternative radial wire array.
Figure 14:
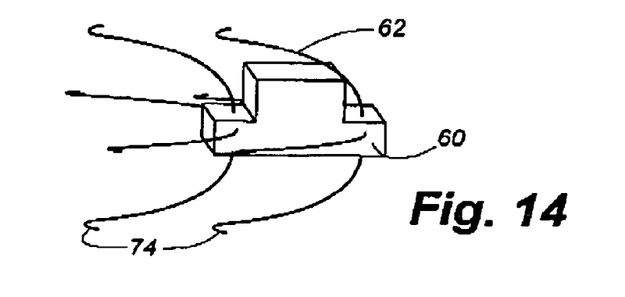
FIG. 14 is an isometric view of a sixth embodiment of an implant assembly of this invention having two radial wire array expansible structures.

The intracorporeal device 60 can be positioned outside a radial wire array 62 so that one end 72 of the intracorporeal device 60 is fixed to a point at or near the apex of the radial wire array 62, as shown in FIG. 12. The intracorporeal device 60 can also be positioned inside the radial wire array so that one end of the device is fixed to a point at or near the apex of the radial wire array, as shown in FIG. 13. In another embodiment, the intracorporeal device may have two radial wire arrays 62 attached to the intracorporeal device 60 so that one end of the intracorporeal device is attached to the apex on the exterior of one of the radial wire arrays and the opposing end of said device is attached to the apex on the interior of the second radial wire array, as shown in FIG. 14.

Figure 15:
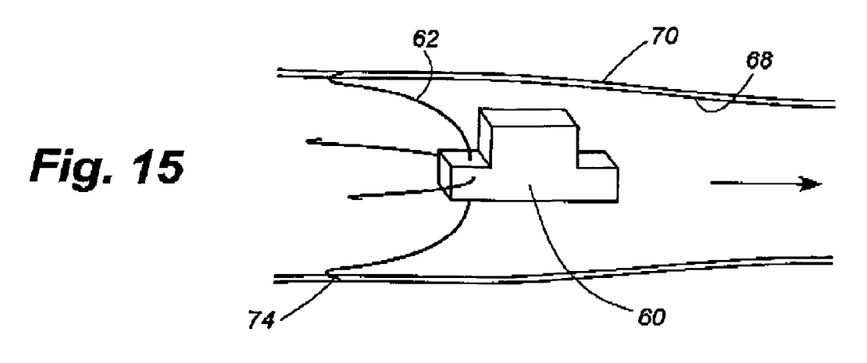
FIG. 15 is an isometric view of the implant assembly of FIG. 12 fixed in a vessel.

In one embodiment, the ends of the radial wire array may terminate with barbs or hooks 74 as shown in FIGS. 12-15. The hooks 74 are turned outwardly with respect to the longitudinal axis of the parabolic profile of the radial wire array 62. The hooks or barbs disposed on the distal ends of the members of the radial wire array prevent the implant assembly from being dislodged after the hooks or barbs have engaged the walls of the vessel, as shown in FIG. 15. The hook or barb features should be of sufficient size to achieve adequate device fixation without perforation or dissection of the vessel wall. Alternatively, the fit of the radial wires within the walls of the vessel may fix the device in the vessel without the use of hooks or barbs, as shown in FIG. 17. The arrows shown in FIGS. 15 and 17 indicate the direction of blood flow.

The wire diameter of the radial wire array lies in the range of about 0.001 to about 0.015 inches. The material comprising the wire can be any biocompatible metal known in the art that possess sufficient elastic properties to be useful for the purpose at hand. The metal may be nitinol, stainless steel, eligiloy, cobalt chrome alloys, or any other suitable metal. The biocompatible wire can optionally be coated with PTFE so as not to pose electromagnetic interference with the function of the intracorporeal device when the device comprises an RF sensor.

Daisy Petal Structures

Figure 20:
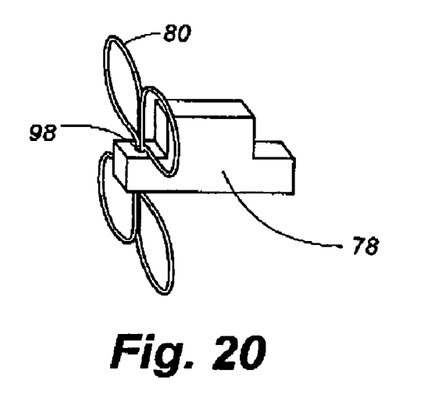
FIG. 20 is an isometric view of a tenth embodiment of an implant assembly of this invention having a daisy petal wire expansible structure.
Figure 21:
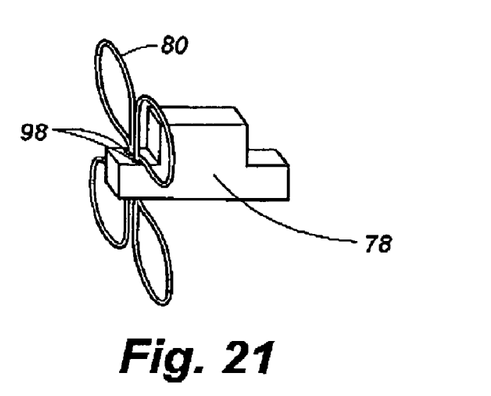
FIG. 21 is an isometric view of an eleventh embodiment of an implant assembly of this invention having a daisy petal wire expansible structure.
Figure 22:
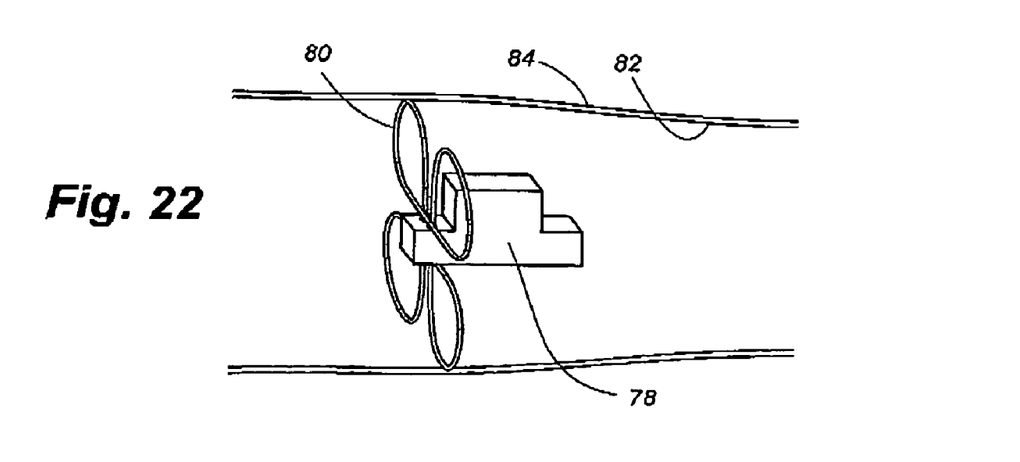
FIG. 22 is an isometric view of the implant assembly of FIG. 18 fixed in a vessel.

An implant assembly according to another aspect of this invention includes an intracorporeal device and an anchoring structure having a daisy petal shape, as shown in FIGS. 18-22. The implant assembly 76 includes an intracorporeal device 78 and a daisy petal wire structure 80, which contacts the inner surface 82 of the wall of the vessel 84, as shown in FIG. 22. The arrow shown in FIG. 22 indicates the direction of blood flow.

Figure 18:
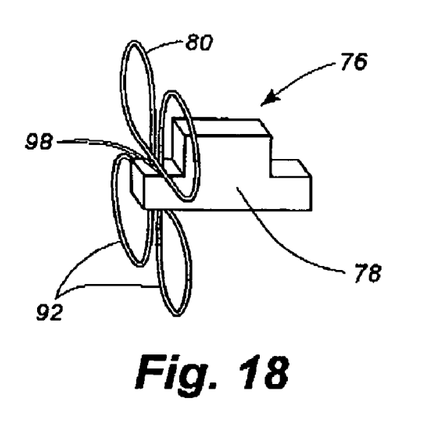
FIG. 18 is an isometric view of an eighth embodiment of an implant assembly of this invention having a daisy petal wire expansible structure.
Figure 19:
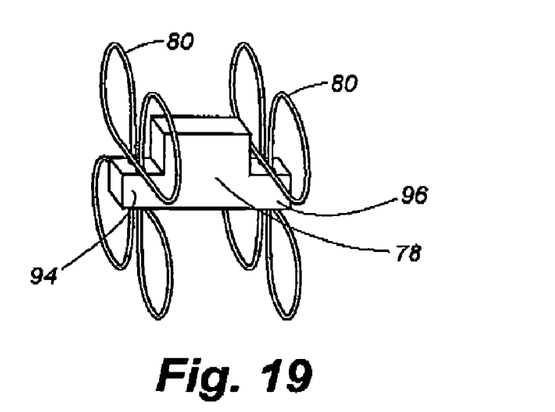
FIG. 19 is an isometric view of a ninth embodiment of an implant assembly of this invention having a daisy petal expansible structure on each end of an intracorporeal device.

The intracorporeal device has a proximal end 86, a distal end 88, and a longitudinal axis 90, as shown in FIG. 18. The daisy petal wire structure 80 is positioned so that the structure lies in a plane normal to the longitudinal axis 90 of the intracorporeal device 78. The daisy petal wire structure 80 may be constructed of a single wire or of a plurality of wires. As shown in FIG. 18, the daisy petal wire structure 80 includes a plurality of lobes 92. The structure may have either an even or an odd number of lobes. As shown in FIG. 19, the intracorporeal device 78 may have two daisy petal wire structures 80 attached to the device on opposing ends 94, 96 and located along the longitudinal axis 90.

The daisy petal wire structure 80 may be attached to the intracorporeal device 78 by threading through a hole 98 located near the edge of the device 78, as shown in FIG. 20. Alternatively, the daisy petal wire structure 80 may be attached to the intracorporeal device 78 by threading through two holes 98 located near the edge of the device 78, as shown in FIGS. 18 and 21.

In one embodiment, the daisy petal wire structure 80 is attached to the intracorporeal device at an anchor point. The anchor is made by crimping a piece of metal to the wire and trimming off the excess wire, so that the crimped-on metal comprises the terminal end of the wire. This metal end also provides a radiopaque marker for fluoroscopic visualization of the device. The wire is threaded through the hole or holes on one end of the sensor and the wire is pulled with sufficient force to bury the anchor fixedly into the silicone coating. The wire is then threaded from top to bottom in a circular fashion, through the hole or holes located on the end of the sensor, to form the daisy petal structure. Upon completion of the daisy petal structure, the free end of the wire is used to create another anchor. The second free end is then pulled back into the silicone coating with sufficient force to bury the second anchor fixedly in the silicone coating. The wire loops are then arranged by mechanical means to create wire members that are substantially evenly distributed radially around the longitudinal axis of the sensor.

The wire diameter in the present invention lies in the range of about 0.001 to about 0.015 inches. The material comprising the wire can be any biocompatible material known in the art that possess sufficient physical properties to be useful for the purpose at hand and such materials are obvious to one skilled in the art. As an example, in a disclosed embodiment, the material is a metal selected from the group comprising nitinol, stainless steel, eligiloy, and cobalt chrome alloys. Optionally, the biocompatible wire may be coated with a dielectric material such as, but not limited to, PTFE, polyurethane, parylene and diamond-like carbon (DLC) so as not to pose electromagnetic interference with the function of the intracorporeal device when the device comprises an RF sensor.

Delivery Systems and Methods

Figure 23:
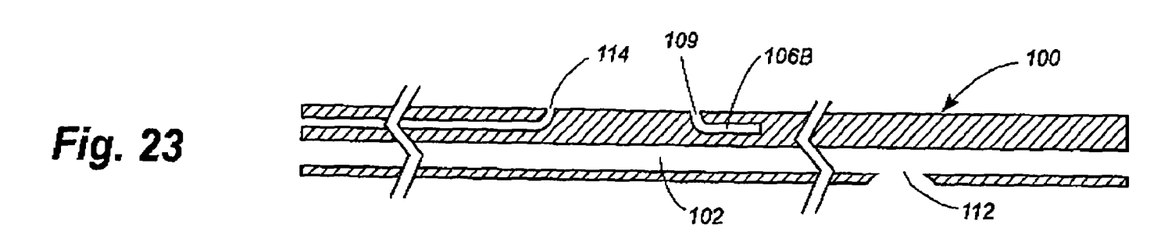
FIG. 23 is a side cross-sectional view of a delivery apparatus of this invention.
Figures 24, 25:
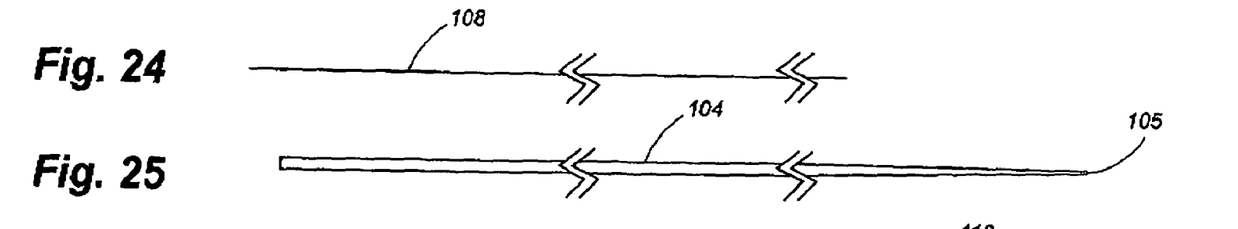
FIG. 24 is a side view of a tether wire of the delivery apparatus of this invention.
FIG. 25 is a side view of a core wire of the delivery apparatus of this invention.
Figures 26, 27:
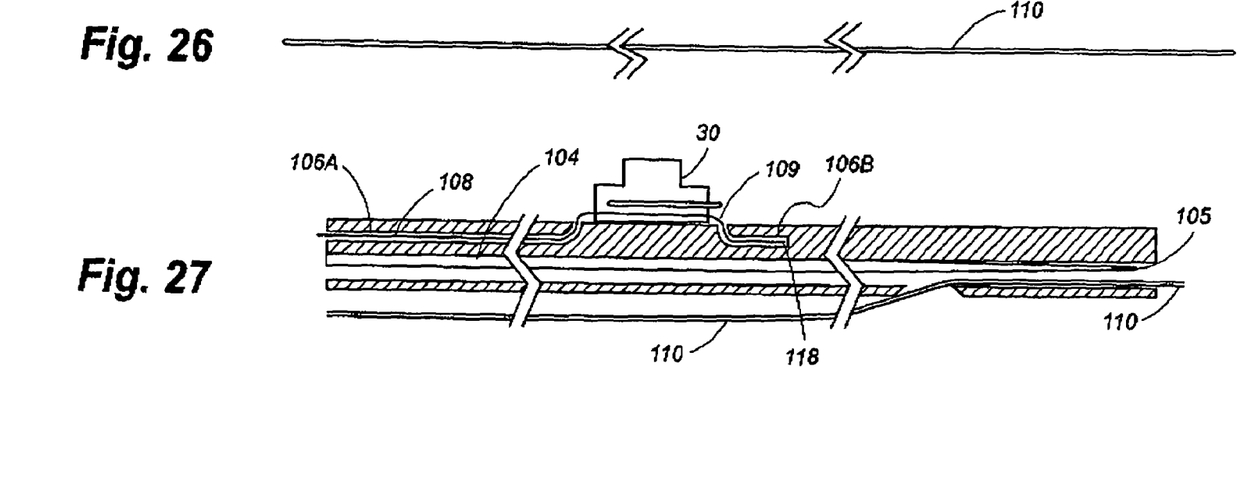
FIG. 26 is a side view of a guidewire of the delivery apparatus of this invention.
FIG. 27 is a side cross-sectional view of the delivery system of this invention comprising the components of FIGS. 23-26.

This invention provides a delivery system for securing, delivering and deploying an implant assembly having an anchoring mechanism coupled to an intracorporeal device. Referring to FIGS. 23-26, the various components of the delivery system are shown individually. As shown in FIG. 23, the delivery apparatus 100 includes a main lumen 102 adapted to accept a core wire 104 (FIG. 25) and a secondary lumen comprising a first section 106A and a second section 106B and adapted to accept a tether wire 108 (FIG. 24). The core wire 104, shown in FIG. 25, provides columnar stiffness to the delivery assembly 100, thereby facilitating advancement of the delivery assembly through the vasculature. Additionally, the core wire 104 also prevents buckling of the delivery assembly 100 when the tether wire is pulled proximally during the implant assembly deployment. The core wire 104 has a decreasing diameter toward its distal end 105, providing gradual decrease in stiffness from the proximal to the distal end of the delivery assembly 100. The tapered core wire 104 can extend past a guidewire aperture 112 in order to reinforce a potential kink point in the delivery apparatus 100 and to facilitate the advancement of the guidewire into the vasculature. The core wire 104 is fixed in the main lumen 102 using adhesive, thermocompression, or any other suitable fixation mechanism. Fixation of the core wire 104 prevents the core wire from being disturbed by the guidewire 110, shown in FIG. 26, when the guidewire 110 enters the main lumen 102 of the delivery apparatus 100 at the guidewire aperture 112 as shown in FIG. 27.

The tether wire 108, shown in FIG. 24, is slidably positioned within the first secondary lumen portion 106A and exits the first secondary lumen portion at an aperture 114 in the wall of the device. As shown in FIG. 27, the tether wire 108 then passes through the coating of the intracorporeal device 30, exiting on the opposite side of the device. The free end 118 of the tether wire 108 enters the second portion 106B of the secondary lumen at the aperture 109.

Figure 28:
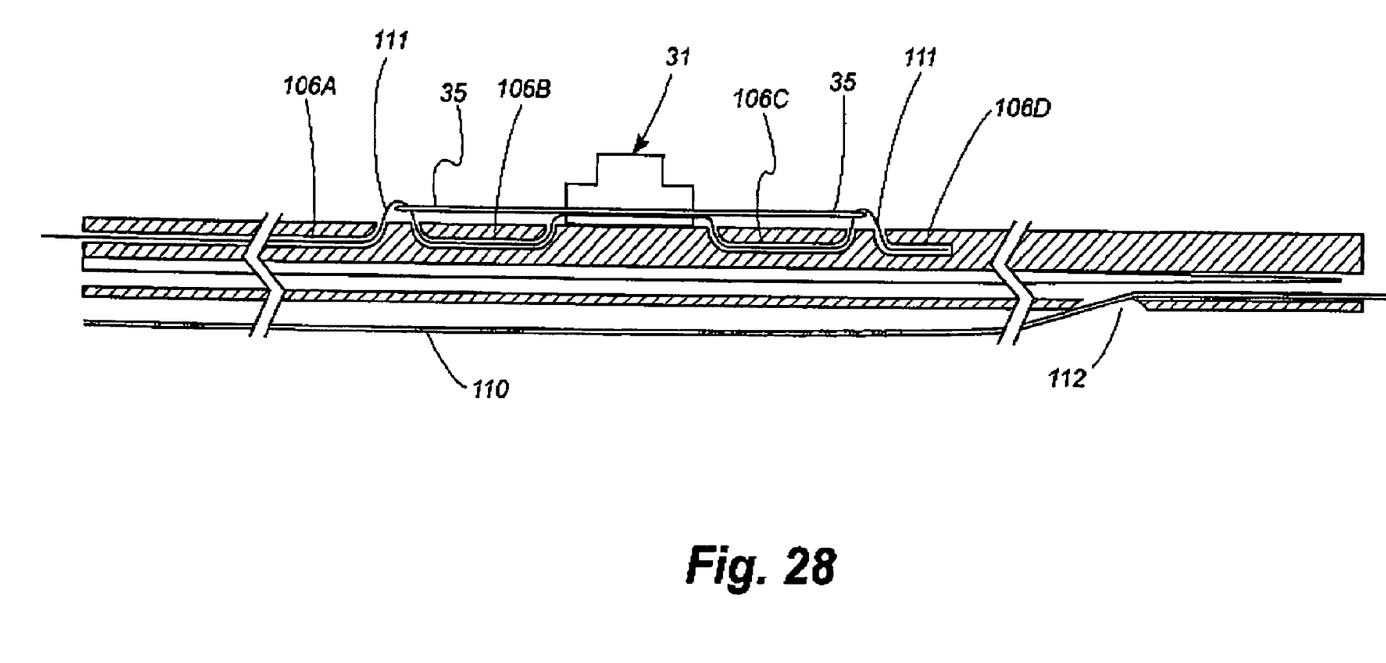
FIG. 28 is a side cross-sectional view of the delivery system of this invention comprising the components of FIGS. 23-26 and the intracorporeal device of FIGS. 4 and 5.

FIG. 28 shows an alternate embodiment of a delivery apparatus adapted to deploy the sensor 31 of FIGS. 4 and 5. Because of the length of the wire loops 35 of the sensor 31, the proximal and distal ends of the loops must be secured to the delivery apparatus so that, when the delivery apparatus curves, the loops will follow the curvature of the delivery apparatus. Toward that end, the secondary lumen of the delivery apparatus of FIG. 28 is divided into four sections 106A-D. The tether wire 108 exits the first section 106A of the secondary lumen and passes over and through wire loops 55 to attach the implant assembly 51 to the delivery apparatus 100. The tether wire then enters the second portion 106B of the secondary lumen. The tether wire then exits the second portion 106B of the secondary lumen and passes through the coating of the sensor 31. The tether wire then enters the third portion 106C of the secondary lumen. Next, the tether wire exits the third portion 106C of the secondary lumen, passes over the wire loop 35, and enters the fourth section 106D of the secondary lumen. Note that with the proximal and distal wire loops 35 thus secured to the delivery apparatus, it is optional as to whether to pass the tether wire 106 through the coating of the body of the sensor 31.

Figure 29:
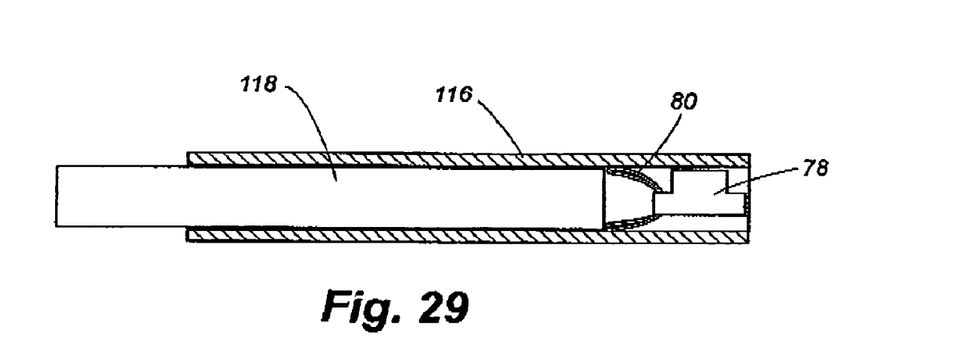
FIG. 29 is a side cross-sectional view of a delivery system of this invention comprising the intracorporeal device of FIGS. 18 and 20.
Figure 30:
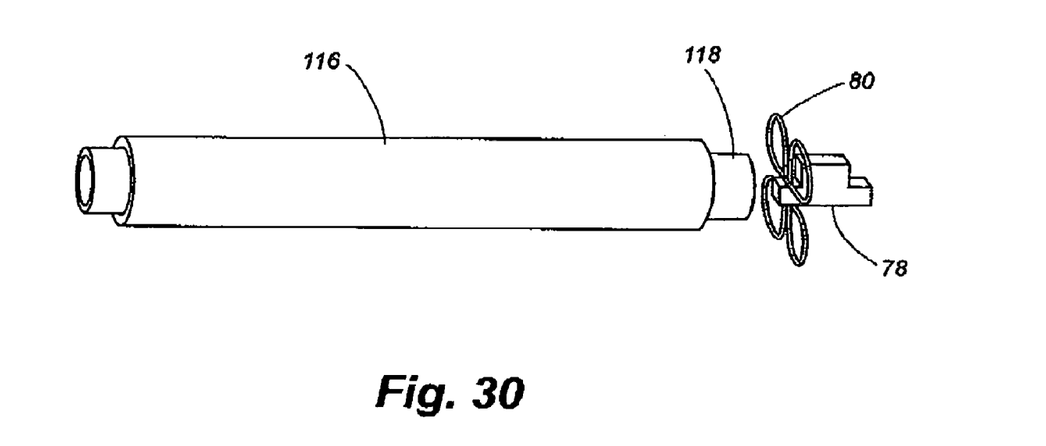
FIG. 30 is an isometric view of the components shown in FIG. 29.

In yet another configuration, shown in FIGS. 29 and 30., an outer sleeve 116 may be provided to constrain an expansible structure 80 of an intracorporeal device 78. The outer sleeve 118 may be slidably positioned over the double lumen tube 118.

Deployment and fixation of an intracorporeal device may be accomplished using either active or passive fixation. In one embodiment, an intracorporeal device is delivered into the vessel and allowed to float in the blood stream until it lodges. After lodging in the vessel, blood flow is maintained due to the configuration of the device and its anchoring structure. In another embodiment, an intracorporeal device includes an anchoring structure that utilizes radial force to fix the device in the vessel. The radial force is released at a selected point of deployment. Preferably the anchoring structure exerts the minimum radial force that will hold the intracorporeal device in place. The radial force may also include the use of hooks or barbs to actively fix the device. In a third embodiment, the intracorporeal device embolizes without an anchor mechanism. It could be preferable to eliminate the need for a securing device and to allow the sensor to reside in a vessel that is small enough to prevent further movement of the sensor. It is suspected that the small size of the sensor would have no deleterious effect on lung function due to the redundancy of blood flow in the lungs at the small vessel level.

One method of deploying and fixing an implant assembly according to this invention is described below. Access is gained into the vasculature and a vessel introducer is positioned in the access site. The access site for the vessel introducer may be the right internal jugular vein, the subclavian artery, the right femoral vein, or any other suitable access site. A guidewire is placed in the vasculature and positioned across the desired deployment site with the aid of, e.g., a Swan-Ganz catheter, a diagnostic catheter or any other suitable catheter, such catheter being removed after the guidewire is in position.

The delivery system is loaded into the vessel introducer and navigated to the deployment site. The delivery system length can be increased or decreased according to standard practice depending on the access site chosen. In one embodiment, the deployment site is a vessel, and may be any artery or arteriole in the pulmonary artery vasculature. After the implant assembly is oriented to a preferred orientation, the implant assembly is deployed by pulling the tether wire proximally to disengage the implant assembly from the delivery apparatus. Upon deployment, the implant assembly is allowed to "float" in the vasculature until it reaches a bifurcation in the vasculature. The anchoring mechanism prohibits the implant assembly from progressing into smaller vessels, thereby lodging the sensor at a location that is immediately proximal to the bifurcation. The delivery assembly and guidewire are then removed from the body.

In an alternative embodiment of this method, an outer sleeve is provided to constrain an expansible structure so that sliding the outer sleeve proximally allows expansion of the expansible structure. If the expansible structure is a radial wire array without hooks or barbs, the implant assembly floats to the next bifurcation where it is lodged in place exactly as described in the previous example. If the radial wire array is equipped with hook or barb features, the implant assembly will remain fixed in the location at which it deployed. The delivery assembly and guidewire are then removed from the body.

The embodiments described above may be employed with a wireless device, as shown in the Figures, or with a wired intracorporeal device.

Finally, it will be understood that the preferred embodiment has been disclosed by way of example, and that other modifications may occur to those skilled in the art without departing from the scope and spirit of the appended claims.

What is claimed is:

1. An implant assembly for deployment into a vessel at a location having an inner diameter D1 and for lodging in the vessel at a downstream location having a smaller inner diameter D2, the implant assembly comprising:
    an intracorporeal device having a first end and a second opposing end, the intracorporeal device body further having a longitudinal axis; and
    a means for passively creating an interference fit between the implant assembly and the inner diameter D2 of the vessel at a position downstream of the location within the vessel having an inner diameter D1, comprising at least one wire loop member, wherein each wire loop member comprises a deformable wire that is fixedly positionally anchored to and extends outwardly longitudinally from at least one end of the intracorporeal device and that is configured to resiliently contact the walls of the vessel, wherein the at least one wire loop member is positioned in an operative plane that is substantially parallel to the longitudinal axis of the intracorporeal device when the wire is in a deployed position,
wherein, in the deployed position, the implant assembly has a diameter less than the inner diameter D1 but greater than or equal to the inner diameter D2, and wherein the intracorporeal device is adapted to be permanently fixed relative to the position of the created interference fit within the vessel.

2. The implant assembly of claim 1, wherein the intracorporeal device comprises a pressure sensor.

3. The implant assembly of claim 1, wherein the at least one wire loop member comprises a single wire having a double loop configuration, wherein the double loop configuration is positioned in the operative plane.

4. The implant assembly of claim 1, wherein at least a portion of the at least one wire loop member has an operative width that is greater than or equal to the inner diameter D2.

5. The implant assembly of claim 1, wherein the at least one wire loop member further comprises a first wire loop extending longitudinally from the first end of said intracorporeal device body.

6. The implant assembly of claim 5, wherein the at least one wire loop member further comprises a second wire loop extending longitudinally from the second end of said intracorporeal device body, wherein that first and second wire loops are substantially co-planar.

7. The implant assembly of claim 1, wherein the intracorporeal device comprises a coating and wherein the ends of the at least one wire loop member are inserted under the coating of the device to attach the at least one wire loop member to the intracorporeal device.

8. The implant assembly of claim 1, wherein the implant assembly is at least partially radiopaque.

9. The implant assembly of claim 8, wherein the implant assembly further comprises a radiopaque marker located at an anchor point.

10. The implant assembly of claim 1, wherein the at least one wire loop member is sufficiently stiff to prevent downstream movement of the implant assembly after the interference fit is created.

11. The implant assembly of claim 10, wherein the implant assembly obstructs less that 50% of the cross-sectional area of the inner diameter of the vessel into which the implant assembly is positioned after the interference fit is created.

12. The implant assembly of claim 1, wherein the at least one wire loop member comprises a single wire having a double loop configuration, and wherein at least a central portion of the single wire is threaded through a hole defined in the intracorporeal device.

13. An implant assembly for deployment in a vessel, the implant assembly comprising:
    an intracorporeal device having a longitudinal axis, and
    a means for passively creating an interference fit between the implant assembly and the inner diameter of the vessel at an operative location downstream of a release location within the vessel, comprising an anchor comprising at least one wire loop member that is substantially positionally anchored relative to a top surface of the intracorporeal device, wherein the at least one wire loop member extends outwardly longitudinally from at least one end of the intracorporeal device in an operative plane that is substantially parallel to the longitudinal axis of the intracorporeal device when the at least one wire loop member is in a deployed position,
wherein at least a portion of the at least one wire loop member is configured to yield to the vessel wall at the operative location, wherein the implant assembly has a width, transverse to the longitudinal axis of the intracorporeal device, that is less than the inner diameter of the vessel at the release location, and wherein, in the deployed position, the at least a portion of the implant assembly has a width, transverse to the longitudinal axis of the intracorporeal device, that is at least equal to the inner diameter of the vessel at the downstream operative location, and wherein the intracorporeal device is adapted to be permanently fixed relative to the operative location in the vessel.

14. The implant assembly of claim 13, wherein the intracorporeal device further comprises a pressure sensor.

15. The implant assembly of claim 13, wherein the at least one wire loop member comprises a single wire having a double loop configuration, wherein the double loop configuration is positioned in the operative plane.

16. The implant assembly of claim 13, wherein at least a portion of the at least one wire loop member has an operative width that is greater than or equal to the inner diameter of the vessel at the downstream operative location.

17. The implant assembly of claim 13, wherein the at least one wire loop member comprises a first wire loop extending longitudinally from the first end of said intracorporeal device body.

18. The implant assembly of claim 13, wherein the at least one wire loop member further a second wire loop extending longitudinally from the second end of said intracorporeal device body, wherein that first and second wire loops are substantially co-planar.

19. The implant assembly of claim 13, wherein the intracorporeal device further comprises a coating and wherein the ends of the at least one wire loop member are inserted under the coating of the intracorporeal device to attach the at least one wire loop member to the intracorporeal device.

20. The implant assembly of claim 13, wherein the implant assembly is at least partially radiopaque.

21. The implant assembly of claim 13, wherein the implant assembly further comprises a radiopaque marker located at an anchor point.

22. The implant assembly of claim 13, wherein the at least one wire loop member is sufficiently stiff to prevent downstream movement of the implant assembly after the interference fit is created at the operative location.

23. The implant assembly of claim 22, wherein the implant assembly obstructs less that 50% of the cross-sectional area of the inner diameter of the vessel into which the implant assembly is positioned after the interference fit is created at the operative location.

24. The implant assembly of claim 11, wherein the vessel is a vessel of the human body.

25. An implant assembly for deployment into a vessel at a location having an inner diameter D1 and for lodging in the vessel at a downstream location having a smaller inner diameter D2, the implant assembly comprising:
an intracorporeal device having a first end and a second opposing end, the intracorporeal device body further having a longitudinal axis;
at least one wire loop member comprising a deformable wire fixedly anchored to and extending outwardly longitudinally from at least one end of the intracorporeal device, wherein the deformable wire is configured to resiliently contact and form an interference fit with a portion of a wall of the vessel, and wherein the at least one wire loop member is positioned in an operative plane that is substantially parallel to the longitudinal axis of the intracorporeal device when the wire is in a deployed position, and wherein, in the deployed position, the implant assembly has a diameter less than the inner diameter D1 but greater than or equal to the inner diameter D2,
wherein the intracorporeal device is adapted to be permanently fixed relative to the position of the created interference fit within the vessel.

26. An implant assembly for deployment in a vessel, the implant assembly comprising:
an intracorporeal device having a longitudinal axis, and
a means for passively creating an interference fit between the implant assembly and the inner diameter of the vessel at an operative location downstream of a release location within the vessel, comprising at least one wire loop member configured to extend outwardly longitudinally from at least one end of the intracorporeal device in an operative plane that is substantially parallel to the longitudinal axis of the intracorporeal device when the at least one wire loop member is in a deployed position,
wherein at least a portion of the at least one wire loop member is configured to yield to the vessel wall at the operative location, and wherein the intracorporeal device is adapted to be permanently fixed relative to the operative location in the vessel.

* * * * *